US012698290B2

(12) United States Patent
Caillot et al.

(10) Patent No.: US 12,698,290 B2
(45) Date of Patent: Aug. 4, 2026

(54) SYNTHETIC METHODS AND INTERMEDIATES FOR PRODUCING COMPOUNDS FOR TREATING KIT- AND PDGFRA-MEDIATED DISEASES

(71) Applicant: Blueprint Medicines Corporation, Cambridge, MA (US)

(72) Inventors: Gilles Caillot, Saint Leu d'Esserent (FR); Khalid Diker, Saint Leu d'Esserent (FR); Brian Heinrich, Cambridge, MA (US); Christopher Lee, Cambridge, MA (US); Hui Li, Cambirdge, MA (US); Baptiste Tournade, Saint Leu d'Esserent (FR); Andreas Wagner, Dottikon (CH)

(73) Assignee: Blueprint Medicines Corporation, Cambridge, MA (US)

( * ) Notice: Subject to any disclaimer, the term of this patent is extended or adjusted under 35 U.S.C. 154(b) by 398 days.

(21) Appl. No.: 18/279,763

(22) PCT Filed: Mar. 3, 2022

(86) PCT No.: PCT/US2022/018692

§ 371 (c)(1),
(2) Date: Aug. 31, 2023

(87) PCT Pub. No.: WO2022/187477

PCT Pub. Date: Sep. 9, 2022

(65) Prior Publication Data

US 2024/0166650 A1 May 23, 2024

Related U.S. Application Data

(60) Provisional application No. 63/155,947, filed on Mar. 3, 2021.

(51) Int. Cl.
*C07D 487/04* (2006.01)

(52) U.S. Cl.
CPC .................................. *C07D 487/04* (2013.01)

(58) Field of Classification Search
CPC .................................................... C07D 487/04
USPC .......................................................... 544/183
See application file for complete search history.

(56) References Cited

U.S. PATENT DOCUMENTS

| | | | |
|---|---|---|---|
| 10,829,493 | B2 | 11/2020 | Dineen |
| 2022/0153748 | A1 | 5/2022 | Kim et al. |

FOREIGN PATENT DOCUMENTS

| | | | |
|---|---|---|---|
| RU | 2706235 | C2 | 11/2019 |
| WO | 2018/183712 | A1 | 10/2018 |
| WO | 2020/210293 | A1 | 10/2020 |
| WO | 2020/210669 | A1 | 10/2020 |

OTHER PUBLICATIONS

Mashkovsky, Medicaments, Moscow. Part 1, p. 8, (1993).

Reichardt, Solute-Solvent Interactions. Solvents and Solvent Effects in Organic Chemistry. Wiley-VCH Verlag GmbH. Chapter 2, pp. 7-64, (2011).

Russian Office Action for Application No. 2023125230, dated Dec. 11, 2025, 12 pages.

Curran, Strategy-Level Separations in Organic Synthesis: From Planning to Practice. Angew Chem Int Ed Engl. May 18, 1998;37(9):1174-1196.

International Search Report and Written Opinion for Application No. PCT/US2022/018692, dated Jul. 8, 2022, 14 pages.

Berge et al., Pharmaceutical salts. J Pharm Sci. Jan. 1977;66(1):1-19.

Clemens et al., Synthesis of benzimidazole based analogues of sphingosine-1-phosphate: discovery of potent, subtype-selective S1P4 receptor agonists. Bioorg Med Chem Lett. Oct. 4, 2004;14(19):4903-6.

Coste et al., Coupling N-Methylated Amino Acids Using PyBroP and PyCloP Halogenophosphonium Salts: Mechanisms and Fields of Application. J Org Chem. 1994;59:2437-2446.

(Continued)

*Primary Examiner* — Charanjit Aulakh

(74) *Attorney, Agent, or Firm* — McCarter & English, LLP; Steven G. Davis; Xin Zhang

(57) ABSTRACT

The present disclosure provides methods and intermediates for making Compound A or a pharmaceutical salt thereof, and/or a solvate of, which are useful as methods and intermediates for producing compounds for treating diseases and conditions related to mutant KIT and PDGFRA.

Compound A

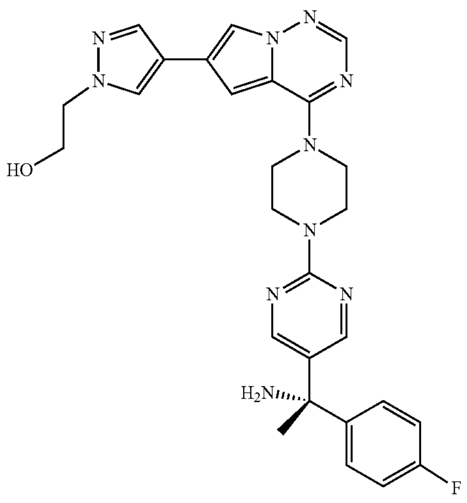

18 Claims, No Drawings

(56) References Cited

OTHER PUBLICATIONS

Janeba et al., Functionalization of guanosine and 2'-deoxyguanosine at C6: a modified Appel process and S(N)Ar displacement of imidazole. Nucleosides Nucleotides Nucleic Acids. 2004;23(1-2):137-47.
Kang et al., Efficient conversion of Biginelli 3,4-dihydropyrimidin-2(1H)-one to pyrimidines via PyBroP-mediated coupling. J Org Chem. Mar. 4, 2005;70(5):1957-60.
Kang et al., Pd-catalyzed direct arylation of tautomerizable heterocycles with aryl boronic acids via C-OH bond activation using phosphonium salts. J Am Chem Soc. Aug. 27, 2008;130(34):11300-2.
Lin et al., Mild and efficient functionalization at C6 of purine 2'-deoxynucleosides and ribonucleosides. Org Lett. Nov. 2, 2000;2(22):3497-9.
Pritz et al., Modification of guanine residues in PNA-synthesis by PyBOP. Tetrahedron Letters. Aug. 14, 2006;47 (33):5893-5896.
Sperry et al., Thermal Stability Assessment of Peptide Coupling Reagents Commonly Used in Pharmaceutical Manufacturing. Org Process Res Dev. 2018;22:1262-1275.
Veliz et al., 6-bromopurine nucleosides as reagents for nucleoside analogue synthesis. J Org Chem. Dec. 14, 2001;66 (25):8592-8.
Veliz et al., C6 substitution of inosine using hexamethylphosphorous triamide in conjunction with carbon tetrahalide or N-halosuccinimide. Tetrahedron Letters. Mar. 11, 2000;41(11):1695-1697.
Wan et al., A Highly Facile and Efficient One-Step Synthesis of N6-Adenosine and N6-2'-Deoxyadenosine Derivatives. Org Lett. 2005;7(26):5877-5880.
Wan et al., The scope and mechanism of phosphonium-mediated S(N)Ar reactions in heterocyclic amides and ureas. J Org Chem. Dec. 21, 2007;72(26):10194-210.
Zhong et al., Structure and synthesis of 6-(substituted-imidazol-1-yl)purines: versatile substrates for regiospecific alkylation and glycosylation at N9. J Org Chem. May 26, 2006;71(11):4216-21.

SYNTHETIC METHODS AND INTERMEDIATES FOR PRODUCING COMPOUNDS FOR TREATING KIT- AND PDGFRA-MEDIATED DISEASES

CROSS-REFERENCE TO RELATED APPLICATIONS

This application is a 35 U.S.C. § 371 national stage filing of International Application No. PCT/US2022/018692, filed on Mar. 3, 2022, which claims priority to U.S. Provisional Application No. 63/155,947, filed Mar. 3, 2021. The entire contents of the aforementioned applications are incorporated herein by reference.

BACKGROUND

This disclosure relates to synthetic intermediates and methods for producing novel pyrrolotriazine compounds that are useful as selective inhibitors of activated KIT and PDGFRA mutant protein kinases. Inhibitors of KIT and PDGFRA mutant protein kinases are useful in producing pharmaceutical compositions, such as, e.g., for the treatment of chronic disorders. The KIT receptor belongs to the class III receptor tyrosine kinase family that also includes the structurally related protein PDGFRA. Normally, stem cell factor binds to and activates KIT by inducing dimerization and autophosphorylation, which induces initiation of downstream signaling. In several tumor types, however, somatic activating mutations in KIT drive ligand-independent constitutive oncogenic activity, including tumor types such as acute myeloid leukemia, melanoma, intercranial germ cell tumors, mediastinal B-cell lymphoma, seminoma, and gastrointestinal stromal tumors. Mutant KIT is also known to play a role in mast cell activation, which is common and possibly necessary for maintenance. Disordered mast cell activation occurs when mast cells are pathologically overproduced or if their activation is out of proportion to the perceived threat to homeostasis. Mast cell activation syndrome refers to a group of disorders with diverse causes presenting with episodic multisystem symptoms as the result of mast cell mediator release. Mastocytosis is one type of mast cell activation syndrome. Compounds of the disclosure are useful for treating mastocytosis. The World Health Organization (WHO) classifies mastocytosis into 7 different categories: cutaneous mastocytosis, indolent systemic mastocytosis (ISM), smoldering systemic mastocytosis (SSM), mastocytosis with an associated hematologic neoplasm (SM-AHN), aggressive systemic mastocytosis (ASM), mast cell leukemia (MCL) and mast cell sarcoma.

Compounds produced by methods of the disclosure can be useful for treating mast cell diseases. Mast cell diseases include mast cell activation syndrome (MCAS) and hereditary alpha tryptasemia (HAT). Other mast cell diseases include mast cell mediated asthma, anaphylaxis (including idiopathic, Ig-E and non-Ig-E mediated), urticaria (including idiopathic and chronic), atopic dermatitis, swelling (angioedema), irritable bowel syndrome, mastocytic gastroenteritis, mastocytic colitis, pruritus, chronic pruritis, pruritis secondary to chronic kidney failure and heart, vascular, intestinal, brain, kidney, liver, pancreas, muscle, bone and skin conditions associated with mast cells.

Compounds produced by methods of the disclosure can also inhibit wild-type KIT. Compounds of the disclosure can be useful for treating mast cell diseases associated with wild type KIT.

U.S. Pat. No. 10,829,493, the entire teachings of which are incorporated herein by reference, discloses the compound shown below (hereinafter the "Compound A") which has highly selective, potent activity against mutant KIT and PDGFRA kinases for the safe and effective treatment of chronic disorders, such as ISM and SSM, as well as other diseases mediated by mutant KIT or PDGFRA.

Compound A

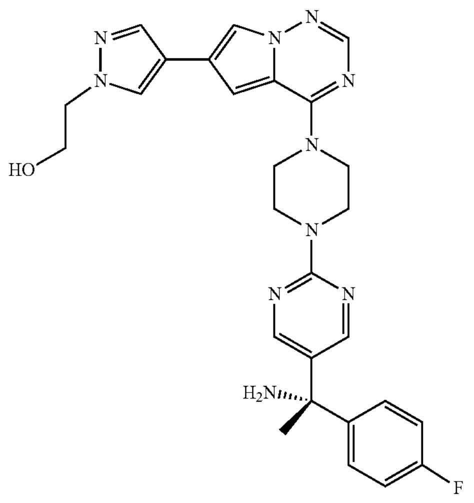

SUMMARY

An object of this disclosure is to provide new synthetic intermediates and methods to prepare Compound A.

Thus, the compounds made by the methods of the disclosure and from the intermediates of the disclosure provide treatments that have desirable efficacy, safety, and pharmaceutical properties for the treatment of KIT- and PDGFRA-mediated diseases. More specifically, Compound A made by the synthetic route of the disclosure exhibits a constellation of beneficial properties including a reduced level of brain penetration, while maintaining efficacy and other desirable pharmaceutical properties relative to other known pyrrolotriazine compounds having mutant KIT and PDGFRA inhibitory activity.

DETAILED DESCRIPTION

It now has been found that the use of phosphonium activating agents for the preparation of Compound A in the coupling of 6-(1-(2-hydroxyethyl)-1H-pyrazol-4-yl)pyrrolo[2,1-f][1,2,4]triazin-4-ol and (tert-butyl 4-(5-((S)-1-(((S)-tert-butylsulfinyl)amino)-1-(4-fluorophenyl)ethyl)pyrimidin-2-yl)piperazine-1-carboxylate) provides a superior process over the use of other coupling agents, which provide slow and/or incomplete reactions and unwanted side reactions (Example 3).

The disclosure provides methods of preparing Compound A. Further, the disclosure provides intermediates in the preparation of Compound A.

A first embodiment is a method of preparing Compound A:

Compound A

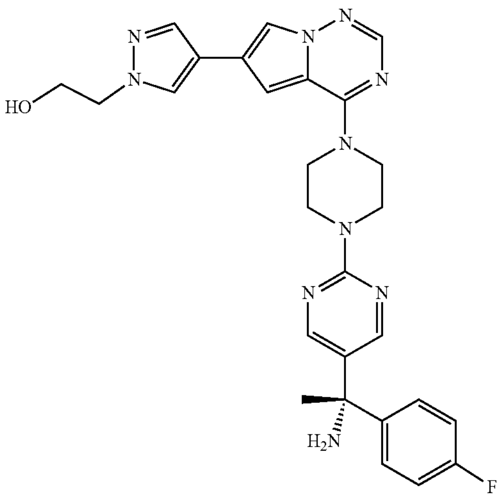

The method comprises reacting a first compound represented by formula (I-1) or a pharmaceutically acceptable acid salt thereof:

(I-1)

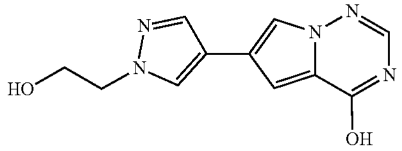

and a second compound represented by formula (II-1) or a pharmaceutically acceptable acid salt thereof:

(II-1)

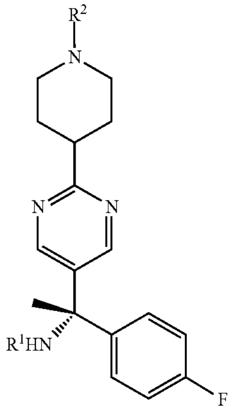

wherein $R^1$ and $R^2$ are each independently selected from H and an amine protecting group, and cleaving the amine protecting groups, if present, to form Compound A. An "amine protecting group" is a chemical moiety that forms a bond with an amine functional group in a molecule to render the amine functional group inert to the conditions of subsequent reaction. After the subsequent reaction is completed, the amine protecting group is removed or cleaved to restore the amine group to its former reactivity. Exemplary protecting groups are found, for example, in Wuts and Greene, Protective Groups in Organic Synthesis, 5th ed., John Wiley & Sons: New Jersey, (2014), which is incorporated herein by reference in its entirety. When R is an amine protecting group, suitable examples include, but are not limited to, Boc ($C(O)OC(CH_3)_3$) or $S(=O)C(CH_3)_3$.

In a second embodiment, the method is as described in the first embodiment, wherein no amine protecting groups are present, i.e., the second compound (II-1) is in its deprotected form $R^1$ is H and $R^2$ is H.

In a third embodiment, the method is as described in the first embodiment, wherein $R^2$ is H and $R^1$ is $S(=O)C(CH_3)_3$.

In a fourth embodiment, the method is as described in the first embodiment, wherein $R^2$ is $C(O)OC(CH_3)_3$ and $R^1$ is $S(=O)C(CH_3)_3$. In a fifth embodiment, the method is as described in the third or fourth embodiment, wherein the amine protecting group (or groups) are removed using acid to form the second compound (II-1) in its deprotected form i.e., $R^1$ and $R^2$ are H. In some aspects, the amine protecting group(s) are removed using an acidic solvent. In some aspects, the amine protecting group(s) are removed using acidic methanol.

In a sixth embodiment, the method is as described in the first, second, third, fourth or fifth embodiment, wherein the reaction is mediated by an agent that activates the aromatic hydroxyl group in the first compound (I-1) for nucleophilic displacement. An agent that activates the aromatic hydroxyl group is an agent that makes the aromatic hydroxyl group more prone to displacement by a nucleophile when the agent is present compared to when the agent is absent. Activation occurs, for example, by the agent reacting with and converting the hydroxyl to a functional group that is more readily displaced by a nucleophile than the hydroxyl group. Examples of agents which activate an aromatic hydroxyl group include carbodiimides, phosphonium salts, aminium salts, uranium/aminium salts, fluoroformamidinium coupling agents, organophosphorus reagents, and triazine coupling reagents.

In a seventh embodiment, the method is as described in the sixth embodiment, wherein the agent is a phosphonium salt.

In an eighth embodiment, the method is as described in the seventh embodiment. Among eight activating agents tested, the phosphonium agents gave the fastest conversion and best yields in the reaction with the lowest levels of by-product formation. Examples of phosphonium agents include (benzotriazol-1-yloxy)tris(dimethylamino)phosphonium hexafluorophosphate (BOP), (benzotriazol-1-yloxy)tris(pyrrolidino)phosphonium hexafluorophosphate (PyBOP), chlorotripyrrolidinophosphonium hexafluorophosphate (PyClOP), 2-(benzotriazol-1-yloxy)-1,3-dimethyl-2-pyrrolidin-1-yl-1,3-diazaphospholidinium hexafluorophosphate (BOMP), (7-azabenzotriazol-1-yloxy)tris(di-methylamino)phosphonium hexafluorophosphate (AOP), (7-azabenzotriazol-1-yloxy)tris(pyrrolidino)phosphonium hexafluorophosphate (PyAOP), 1-cyano-2-ethoxy-2-oxoethylideneaminooxy-tris-pyrrolidino-phosphonium hexafluorophosphate (PyOxim), or bromotripyrrolidinophosphonium hexafluorophosphate (PyBrOP).

In a ninth embodiment, the method is as described in the sixth, seventh, or eighth embodiments, wherein the agent is PyBOP or PyClOP. In one aspect, the agent is PyBOP. In another aspect, the agent is PyClOP. The agents PyBOP and PyClOP gave better yields, higher purity products, less exotherm while adding than other phosphonium agents.

PyClOP has the added advantage of being highly reactive, safe, and avoids the release of toxic HMPA.

In a tenth embodiment, the method is as described in the sixth, seventh, eighth, or ninth embodiments, wherein the agent which activates the aromatic hydroxyl group is present in a molar excess relative to moles of the first compound (I-1), for example, a 1.3 to 1.8 molar excess. "Molar excess" is the moles of the agent present in the reaction divided by the moles of the first compound (I-1) present in the reaction. In some examples, the agent is present in a 1.3 to 1.7 molar excess, a 1.3 to 1.6 molar excess, a 1.3 to 1.5 molar excess, a 1.4 to 1.5 molar excess, or a 1.4 to a 1.6 molar excess. In some examples, the agent is present in a 1.3 molar excess, a 1.4 molar excess, a 1.5 molar excess, 1.6 molar excess, 1.7 molar excess or 1.8 molar excess.

In an eleventh embodiment, the method is as described in the first, second, third, fourth, fifth, sixth, seventh, eighth, ninth, or tenth embodiments, wherein the reacting takes place in the presence of a non-nucleophilic base. A non-nucleophilic base is a sterically hindered basic molecule that is a poor nucleophile. In some examples, the non-nucleophilic base is an amine non-nucleophilic base. In some examples, the amine non-nucleophilic base is selected from the group consisting of 1,8-diazabicyclo(5.4.0)undec-7-ene (DBU), diisopropylethylamine (DIPEA), dimethylaminopyridine (DMAP), and triethylamine (TEA). In some examples, the amine non-nucleophilic base is 1,8-diazabicyclo(5.4.0)undec-7-ene (DBU). In other examples, the amine non-nucleophilic base is triethylamine (TEA).

In a twelfth embodiment, the method is as described in the eleventh embodiment, wherein the non-nucleophilic amine base is DBU, and the agent which activates the aromatic hydroxyl group is PyBOP. PyBOP was tested in combination with five non-nucleophilic amine bases, and the PyBOP/DBU combination resulted in the most rapid conversion rates and the highest yields with fewer impurities.

In a thirteenth embodiment, the method is as described in the eleventh embodiment, wherein the non-nucleophilic amine base is TEA, and the agent which activates the aromatic hydroxyl group is PyClOP. PyClOP was tested with DBU and with TEA. The PyClOP/TEA combination resulted in cleaner reaction profiles and better control of critical impurities (Example 4). The reaction byproduct of TEA is also less soluble in the reaction mixture with acetonitrile as the solvent, which allows for the advantage of a facile isolation of product by crystallization.

In a fourteenth embodiment, the method is as described in the first, second, third, fourth, fifth, sixth, seventh, eighth, ninth, tenth, or eleventh embodiments, wherein the second compound is a pharmaceutically acceptable acid salt of the compound of formula (II-1). Examples of pharmaceutically acceptable acid salts include the hydrobromide, hydrochloride, sulfate, bisulfate, phosphate, nitrate, acetate, valerate, oleate, palmitate, stearate, laurate, benzoate, lactate, tosylate, citrate, maleate, fumarate, succinate, tartrate, naphthylate, mesylate, glucoheptonate, lactobionate, and laurylsulphonate salts and the like.

In a fifteenth embodiment, the method is as described in the fourteenth embodiment, wherein the pharmaceutically acceptable acid salt of the compound of formula (II-1) is an HCl salt. In comparison to several other salts tested, the HCl salt of formula (II-1) provided higher yields, faster conversions and fewer impurities than other salts tested, for example an HCl salt comprising 3.5 moles of HCl per mole of compound (II-1).

In a sixteenth embodiment, the method is as described in the first, second, third, fourth, fifth, sixth, seventh, eighth, ninth, tenth, or eleventh embodiments, wherein the second compound is the free base of the compound of formula (II-1).

In a seventeenth embodiment, the method is as described in the fourteen, fifteenth, or sixteenth embodiments, wherein the amine non-nucleophilic base is present in a molar excess relative to the moles of the first compound (I-1), for example, a 5.0 to 12.0 molar excess. In some examples, the amine non-nucleophilic base is present in a 5.0 to 6.5 molar excess, a 5.0 to 6.0 molar excess, a 9.0 to 10.5 or a 9.0 to 10.0 molar excess, relative to the moles of the first compound (I-1). In some examples, the amine non-nucleophilic base is present in a 5.5 molar excess, a 6.0 molar excess, a 6.5 molar excess, a 7.0 molar excess, an 8.5 molar excess, a 9.0 molar excess, a 9.5 molar excess, a 10.0 molar excess, a 10.5 molar excess, or a 12.0 molar excess relative to the moles of the first compound (I-1). In one aspect, the agent which activates the aromatic hydroxyl group is PyBOP, the non-nucleophilic amine base is DBU and DBU is used in a 5.3 to 5.7 molar excess relative to the first compound (I-1) (such as a 5.5 molar excess). This quantity of DBU provides a rapid, nearly quantitative conversion at high yield under mild conditions with minimal impurities. In one aspect, the agent which activates the aromatic hydroxyl group is PyClOP, the non-nucleophilic amine base is TEA and TEA is used in a 10.3 to 10.7 or 11.8 to 12.2 molar excess relative to the first compound (I-1)(such as a 10.5 or 12.0 molar excess). This quantity of TEA also provides a rapid nearly quantitative conversion at high yield with minimal impurities. PyClOP is used in a molar excess of 1.5 to 1.7 (such as 1.6 molar excess) relative to the first compound (I-1).

In an eighteenth embodiment, the method as described in the first, second, third, fourth, fifth, sixth, seventh, eighth, ninth, tenth, eleventh, twelfth, thirteenth, fourteenth, fifteenth, sixteenth, or seventeenth embodiments, wherein the first compound (I-1) and the second compound (II-1) are dissolved in a first solvent to form a solution. Suitable solvents can be readily selected by one of skill in the art of organic synthesis. Suitable solvents are substantially non-reactive with the starting materials (reactants), intermediates, or products at the temperatures at which the reactions are carried out and do not substantially interfere with the reaction. A given reaction can be performed in one solvent or a mixture of more than one solvent. Examples of suitable first solvents include acetonitrile ($CH_3CN$), dimethylformamide (DMF), an ethanol/water mixtures, 2-methyl tetrahydrofuran (2-MeTHF), tetrahydrofuran (THF), dichloroethane (DCE), dioxane and dimethylaminopyridine (DMAP). In one aspect, the first solvent is acetonitrile ($CH_3CN$). Using acetonitrile as the first solvent allows for a homogeneous reaction mixture and also for direct isolation of Compound A by crystallization from the reaction mixture by adding water as an antisolvent. The majority of the reaction byproducts remain dissolved in the acetonitrile-water mother liquor while Compound A, which has low solubility, crystallizes from solution.

In a nineteenth embodiment, the method is as described in the first, second, third, fourth, fifth, sixth, seventh, eighth, ninth, tenth, eleventh, twelfth, thirteenth, fourteenth, fifteenth, sixteenth, seventeenth, or eighteenth embodiments, wherein reacting is conducted at a temperature of 15-100° C. In some examples, reacting is conducted at a temperature of 20-50° C., 30-40° C., 15-25° C., 25-35° C., 45-55° C., 55-65° C., 65-75° C., 75-85° C., 80-90° C. or 90-100° C. In another aspect, the temperature is between 20 to 30° C. (such as room temperature, e.g., 25±3° C.) when the activating agent is PyBOP and the base is DBU. In another aspect, the temperature is between 80 to 90° C. (such as 85° C.) when the activating agent is PyClOP and the base is TEA.

In a twentieth embodiment, the method is as described in the eighteenth or nineteenth embodiments, wherein the agent is added to the solution of the first compound (I-1) and the second compound (II-1) dissolved in a first solvent. In some aspects, the agent is added over a period of time ranging from 5 to 120 minutes. In some examples, the agent is added over a period of time ranging from 10 to 100 minutes, 20 to 80 minutes, 30 to 60 minutes, 5 to 30 minutes, 30 to 60 minutes, 60 to 90 minutes, or 90 to 120 minutes. In some examples, the agent must be added to the solution of the first compound (I-1) and the second compound (II-1) to provide consistent and reproducible results to produce Compound A on a large scale. In one aspect, the agent must be added to the solution, when the agent is PyBOP.

In a twenty-first embodiment, the method is as described in the eleventh, twelfth, thirteenth, fourteenth, fifteenth, sixteenth, seventeen, eighteenth, nineteenth, or twentieth embodiment, wherein the non-nucleophilic amine base is added prior to the addition of the first solvent. In some examples, following removal of the amine protecting groups in acidic methanol, TEA is added prior to the addition of $CH_3CN$. When TEA is not added prior to the addition of $CH_3CN$, there are issues with crust formation in the reactor and a significant formation of the impurity (Example 2/Table 1)

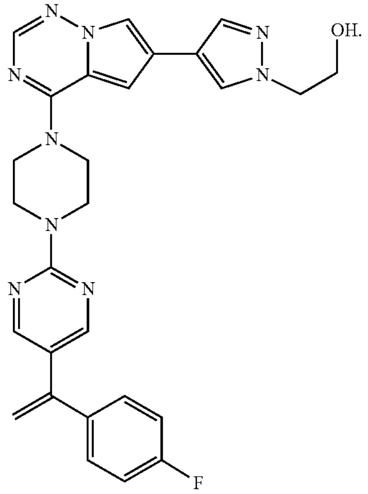

In a twenty-second embodiment, the method as described in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, or twenty-first embodiments, wherein activated charcoal is added. The addition of activated charcoal improves the purity and color of the resulting Compound A.

A twenty-third embodiment is a compound of Formula (I-1):

(I-1)

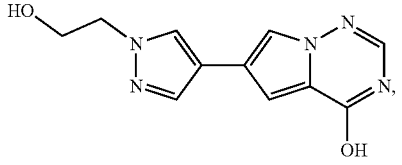

or a pharmaceutically acceptable salt thereof. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Representative pharmaceutically acceptable salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, e.g., Berge et al. (1977) "Pharmaceutical Salts", J. Pharm. Sci. 66: 1-19.)

A twenty-fourth embodiment is a method of purifying Compound A:

Compound A

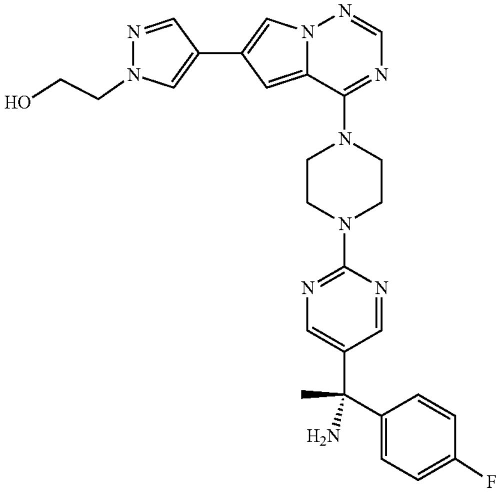

comprising:

converting Compound A to an acid salt;

removing impurities from the acid salt; and basifying the acid salt to prepare a purified Compound A.

In a twenty-fifth embodiment, the method is as described in the twenty-fourth embodiment, wherein Compound A is converted to a phosphate salt by reacting Compound A with phosphoric acid.

In a twenty-sixth embodiment, the method is as described in the twenty-fourth or twenty-fifth embodiment, wherein Compound A is converted to the acid salt by dissolving Compound A in an aqueous solution and adding at least one equivalent of the acid.

In a twenty-seventh embodiment, the method is as described in the twenty-sixth embodiment, wherein impurities are removed from the acid salt by washing the aqueous solution with an organic solvent immiscible with the aqueous solution. In a specific embodiment, the organic solvent is 2-methyl tetrahydrofuran.

In a twenty-seventh embodiment, the method is as described in the twenty-fourth, twenty-fifth, twenty-sixth embodiment, wherein impurities are removed from the acid salt with activated charcoal.

In a twenty-eighth embodiment, the method is as described in the twenty-fourth, twenty-fifth, twenty-sixth, or twenty-seventh embodiment, wherein the aqueous solution is basified with aqueous base to precipitate Compound A. In a specific embodiment, the aqueous base is aqueous hydroxide, e.g., sodium hydroxide.

In a twenty-ninth embodiment, the method is as described in the twenty-fourth, twenty-fifth, twenty-sixth, twenty-seventh, or twenty-eighth embodiment, wherein Compound A is the compound produced by the method of any one of the first through twenty-second embodiments disclosed herein.

The disclosure is illustrated by the following examples, which are not intended to be limiting in any way.

EXEMPLIFICATION

Synthetic Preparations

Example 1A: Preparation of Intermediate (I-1) With DTBPF

Preparation 1A: 6-(1-(2-hydroxyethyl)-1H-pyrazol-4-yl)pyrrolo[2,1-f][1,2,4]triazin-4-ol (I-1)

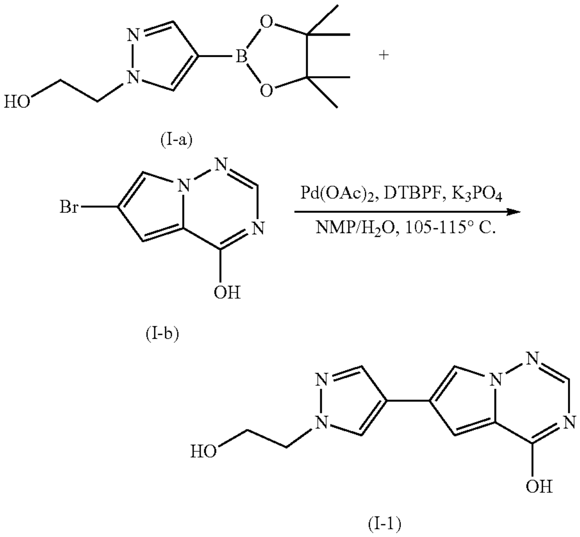

Synthesis of 6-(1-(2-hydroxyethyl)-1H-pyrazol-4-yl)pyrrolo[2,1-f][1,2,4]triazin-4-ol (I-1): (I-a) (2-(4-(4,4,5,5-tetramethyl-1,3,2-dioxaborolan-2-yl)-1H-pyrazol-1-yl)ethan-1-ol) (5 kg) and (I-b) (6-bromopyrrolo[2,1-f][1,2,4]triazin-4-ol) (11.1 kg, 2 eq) were combined and agitated in N-methyl-2-pyrrolidone (NMP) (20 L) at 20-30° C. To this mixture was added palladium(II) acetate (105 g, 0.02 eq), 1,1'(di-tert-butylphosphino)ferrocene (222 g, 0.02 eq), and 50%-w/w aqueous tripotassium phosphate ($K_3PO_4$) solution (60 kg, 6 eq). The reaction was heated at 105-115° C. After 2 h, the reaction was cooled to 60-80° C. and transferred to a second vessel containing a mixture of N-acetyl-L-cysteine (760 g, 0.20 eq) and ethylenediaminetetraacetic acid disodium salt dihydrate (780 g, 0.09 eq) in water (42 kg). The resulting mixture was agitated at 45-55° C. for 30 minutes and then allowed to settle 30 minutes to separate and remove the aqueous phase. The resulting organic layer was diluted with water (50 kg) and pH adjusted to 6.3 to 7.5 with aqueous hydrochloric acid. After the addition of seed crystals (10 g) at 45-55° C., crystals were observed, and the mixture was cooled to 5-15° C. The solid crystals were isolated by filtration and washed with water (3×15 kg) followed by isopropyl alcohol (4×12 kg). The solid was dried at 60° C. to give 4.3 kg, 75% yield and 99.1%-w/w purity.

Example 1B: Preparation of Intermediate (I-1)

Preparation 1B: 6-(1-(2-hydroxyethyl)-1H-pyrazol-4-yl)pyrrolo[2,1-f][1,2,4]triazin-4-ol (I-1)

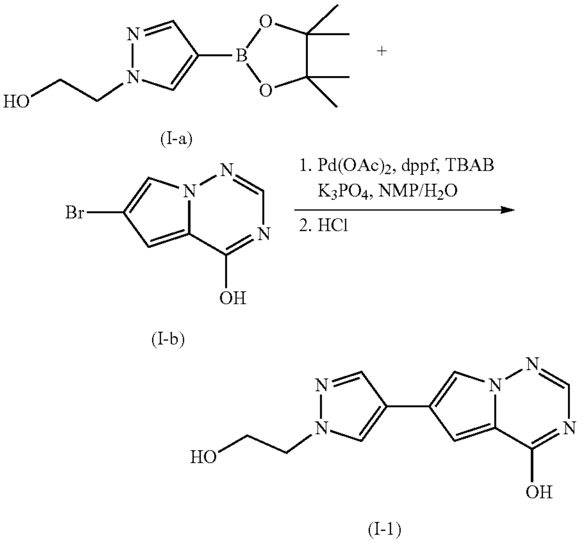

To a reactor was charged N-methyl-2-pyrrolidone (NMP) (52.7 L), (I-b)(10.55 kg 1.0 equiv), (I-a) (23.5 kg, 2.0 equiv), tetra-N-buytlammonium bromide ($n-Bu_4NBr$ also referred to as "TBAB") (636 g, 0.04 equiv), palladium(II) acetate ($Pd(OAc)_2$) (221.2 g, 0.02 equiv), 1,1'-bis(ferrocenediyl-bis (diphenylphosphine (dppf) (548 g, 0.02 equiv) and degassed with $N_2$. Next a $N_2$ degassed solution of tripotassium phosphate ($K_3PO_4$) (62.8 kg, 6.0 equiv) in water (63 L) was added and the batch was heated to reflux at ~110° C. After 2 hours at reflux, the reaction was sampled for conversion of (I-b) to (I-1) (IPC conversion: 99.4%; target≥95% conversion). The batch was then cooled to ~59° C. and water (105.5 L) was added. The batch was cooled to ~29° C. and filtered through a pad of Celite® (7 kg) followed by a water rinse (21.1 L×2). The product was then precipitated from the filtrate by adding a solution of 6 M HCl (46.5 kg, 8.5 equiv) to reach pH 6-7 while maintaining 15-30° C. The slurry was cooled to 5-15° C. and held for 3 days, then was cooled to (−)5-5° C. and held for 2 hours prior to isolation. The (I-1) product is isolated by filtration, washed with pre-cooled (−)5-5° C. water (31.7 L×2) and de-liquored.

The (I-1) wet cake is added to a reactor and triturated with water (105.5 L) at 60-65° C. for a minimum of 1 hour, followed by cooling to 20-25° C. (I-1) was isolated by filtration, washed with 15-25° C. water (21.1 L×2) and de-liquored. A sample was analyzed for residual pinacol (0.02%) and (I-b) (0.1%). The wet cake was dried using a vacuum oven at 60° C. for ~4.5 days to give 9.41 kg of the title compound with 78% yield and 99.8% purity.

Example 1C: Alternative Preparation of Intermediate (I-1)

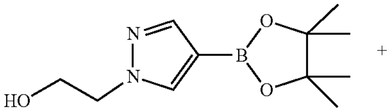

(I-a)

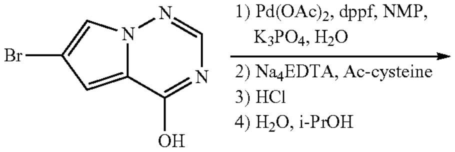

(I-b)

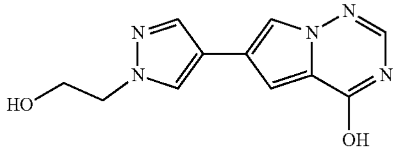

(I-1)

To a reactor was charged NMP (1200 mL), (I-a) (667.5 g, 1.0 equiv), (I-b) (300 g, 2.0 equiv), dppf (15.5 g, 0.02 equiv.)

and $Pd(OAc)_2$ (6.3 g, 0.02 equiv.). The mixture was degassed with $N_2$. To same reactor was added degassed solution of $K_3PO_4$ (1785 g, 6.0 equiv.) in water (1872 mL). The mixture was heated to 75° C. and stirred for 2 h, cooled to ambient temperature for stirring overnight, then heated to 110° C. and stirred for 3 h (IPC by HPLC showed 97.8% conversion). The mixture was cooled to 20-25° C., which was followed by addition of water (3000 mL), EDTA tetrasodium salt hydrate (52.5 g, 0.09 equiv.), N-acetyl cysteine (45.8 g, 0.2 equiv.). The mixture was stirred for 3 h and the organic layer was separated from the aqueous layer. The organic layer was heated to 45-55° C. Concentrated HCl (10.6 N, 285 mL) was added to adjust the pH to 6.84. To the mixture at ~50° C. was added compound (I-1) seed (1.5 g, 0.5% w/w), which was followed by cooling the mixture to 5-15° C. and stirring for 1.5 h. The slurry was filtered and the wet cake was charged to a reactor, followed by addition of water (3000 mL). The slurry was again filtered and the wet cake was charged to a reactor, followed by addition of i-PrOH (3000 mL). The slurry was filtered, washed with i-PrOH (900 mL×2). The wet cake was dried at 50° C. under vacuum to give 189 g of compound (I-1) as a solid, with 55% yield, 98.6% HPLC purity, 97.8 wt % by quantitative NMR assay.

Example 2: The Timing of the Addition of Triethylamine

Example 2A: Preparation of Compound A From Intermediate (I-1) With PyClOP and TEA Preparation 2A: (S)-2-(4-(4-(4-(5-(1-amino-1-(4-fluorophenyl)ethyl)pyrimidin-2-yl)piperazin-1-yl) pyrrolo[2,1-f][1,2,4]triazin-6-yl)1H-pyrazol-1-yl) ethan-1-ol (Compound A)

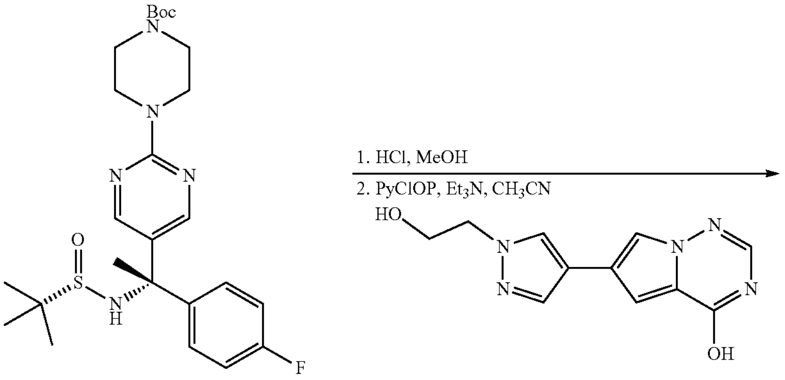

(I-c)

(I-1)

-continued

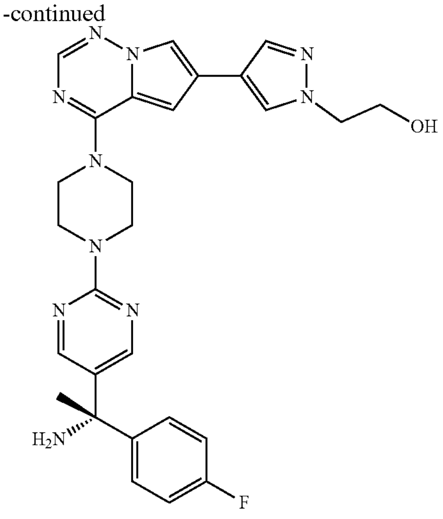

Compound A

Compound (I-c) can be prepared based on the procedure disclosed in International Application Publication No. WO2020/210293 and WO2020/210669, the entire teachings of which are incorporated herein by reference. A mixture of (I-c) (tert-butyl 4-(5-((S)-1-(((S)-tert-butylsulfinyl)amino)-1-(4-fluorophenyl)ethyl)pyrimidin-2-yl)piperazine-1-carboxylate) (27.2 kg, 1.10 eq) and hydrogen chloride (8.8 kg, 4.95 eq) was agitated at 35-45° C. in methanol (239 L) for 2 h. At this time, the reaction was refluxed under reduced pressure for 2 h and then cooled to 20-30° C. The methanol solvent was replaced with acetonitrile via a solvent swap. Specifically, the methanolic solution was transferred to a vessel containing acetonitrile (168 L) and the mixture was distilled at 70-85° C., while maintaining the volume by adding additional acetonitrile. After cooling to 15-25° C., triethylamine (TEA) (71 L, 10.5 equiv.) was added and after 30 minutes the solid byproduct was removed by filtration. To the remaining solution, acetonitrile (48 L), (I-1) (6-(1-(2-hydroxyethyl)-1H-pyrazol-4-yl)pyrrolo[2,1-f][1,2,4]triazin-4-ol) (12 kg, 1 eq), and chlorotripyrrolidinophosphonium hexafluorophosphate (PyClOP, 33 kg, 1.6 eq) were added. The reaction was heated at 70-85° C. for 4 h, then cooled to 55-65° C. and seeded with Compound A freebase. After cooling to 0-10° C. over 5 h and holding for 15 h, the solid product was isolated by filtration. The filter cake was washed with acetonitrile (37 kg) and water (5×48 kg). After drying 15.0 kg of Compound A was isolated in 58% yield and 96.6% purity.

Example 2B: Preparation of Compound A From Intermediate (I-1) by Charging TEA Prior to the Addition of $CH_3CN$ Preparation 2B: (S)-2-(4-(4-(4-(5-(1-amino-1-(4-fluorophenyl)ethyl)pyrimidin-2-yl)piperazin-1-yl)pyrrolo[2,1-f][1,2,4]triazin-6-yl)1H-pyrazol-1-yl)ethan-1-ol (Compound A)

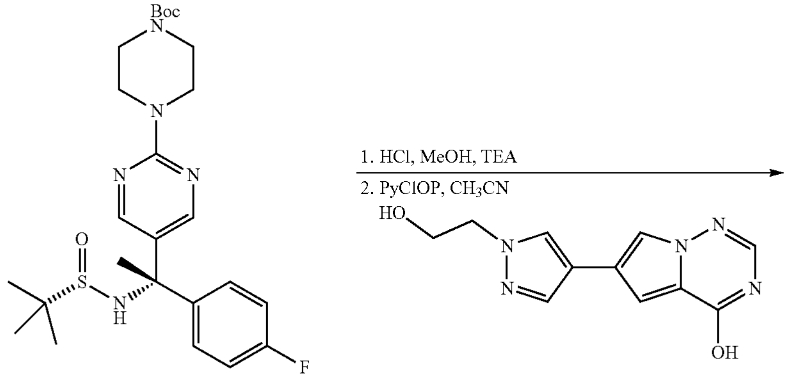

(I-c)

(I-1)

-continued

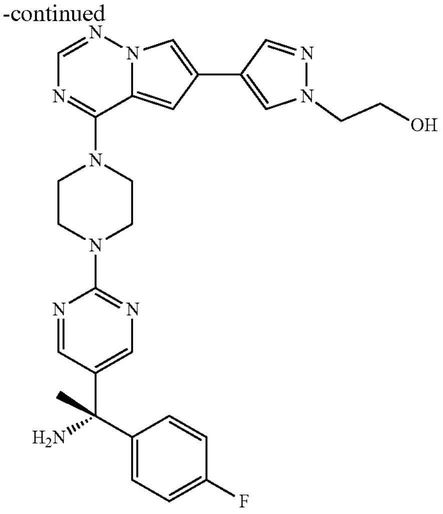

Compound A

To a reactor R1 at 15-25° C. was charged methanol (136 mL), (I-c) (22.7 g, 1.10 equiv.). Hydrogen chloride gas (7.36 g, 4.95 equiv.) was then charged to R1 at 15-45° C. The resulting mixture was stirred at 35-45° C. for at least 2 h until in-process control (IPC) shows completion of reaction. Methanol (50 mL) was then charged to R1, which was followed by distillation at 35-45° C. at reduced pressure to remove ~50 mL of methanol. Triethylamine (TEA, 28.4 mL, 5 equiv.) was added to R1 at 25-45° C. to adjust pH≥8 prior to addition of $CH_3CN$. The mixture in R1 was distilled at 60-85° C. at atmospheric pressure to remove ~30 mL methanol distillate. The distillation was continued at atmospheric pressure under parallel feed of acetonitrile (~300 mL) and maintained constant volume by removing ~300 mL distillate. Another ~40 mL distillate was removed afterwards at 75-85° C. A 2$^{nd}$ portion of TEA (38.9 mL, 7 equiv.) was charged to R1 at 70-85° C. The mixture was cooled to 15-25° C. and filtered (filtrate collected in reactor R2). Acetonitrile (10 mL) was charged to R1 and rinse via the polish filter into R2.

To R2 at 15-30° C. was charged (I-1) (10.0 g, 1.00 equiv.), PyClOP (27.5 g, 1.60 equiv.). Acetonitrile (10 mL) was added to rinse the dosage system. The mixture in R2 was heated to 70-85° C. and stirred for at least 4 h until IPC shows completion of reaction. The reaction mixture was cooled to 55-65° C., which was followed by charging of Compound A seed crystals (0.17 g) at 50-60° C. and stirring for at least 15 min. The mixture in R2 was cooled to 0-10° C. during at least 5 h and stirred for at least 1 h at 0-10° C. The resulting suspension was filtered. The wet cake was washed sequentially with acetonitrile (40 mL), deionized water (40 mL×2), then dried under vacuum at 45-55° C. to give 16.6 g Compound A free base as a solid, with 77% yield, 98.9% HPLC purity.

TABLE 1

Comparison of Impurity Profiles of Compound A using Different Processes

| Process | Impurity (a/a %)<br>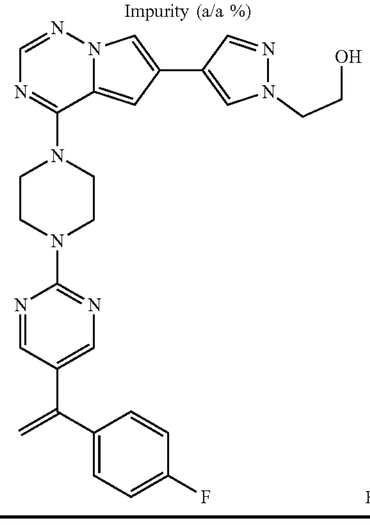 | Remarks |
|---|---|---|
| Example 2A<br>(TEA added after $CH_3CN$) | 3.4% | thick crust formation<br>during solvent swap |

TABLE 1-continued

Comparison of Impurity Profiles of Compound A using Different Processes

| Process | Impurity (a/a %) 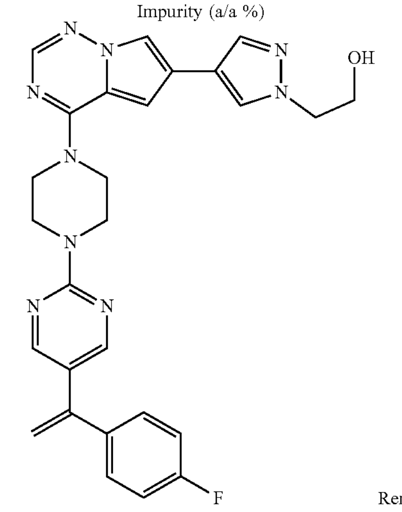 | Remarks |
|---|---|---|
| Example 2B (TEA added prior to $CH_3CN$) | 0.16-0.41 | no crust formation during solvent swap |

Example 2C: Preparation of Compound A From Intermediate (I-1) With PyBOP and DBU

Preparation 2C: (S)-2-(4-(4-(4-(5-(1-amino-1-(4-fluorophenyl)ethyl)pyrimidin-2-yl)piperazin-1-yl)pyrrolo[2,1-f][1,2,4]triazin-6-yl)1H-pyrazol-1-yl)ethan-1-ol (Compound A)

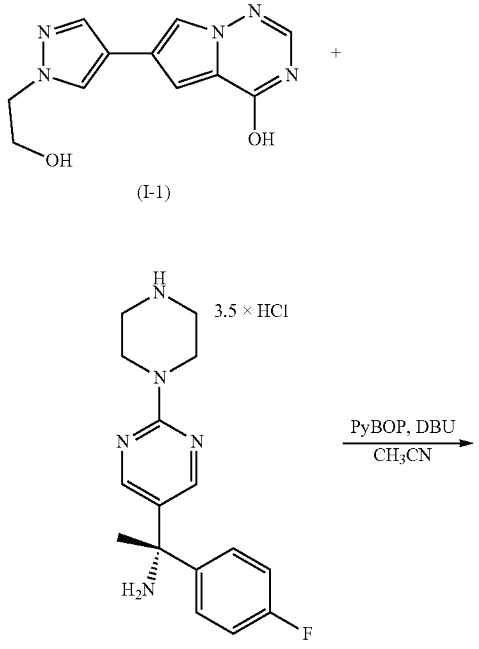

(I-1)

(II-2)

-continued

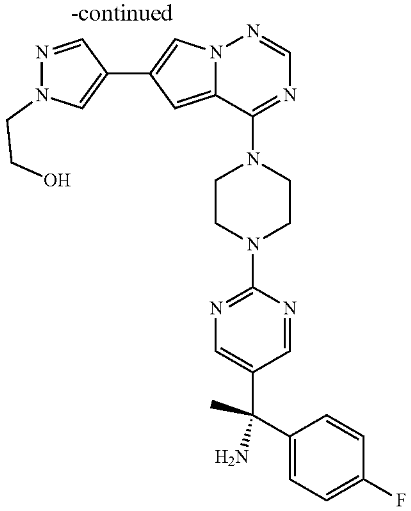

Compound A

To a reactor (R1) was charged acetonitrile ($CH_3CN$, 40 L), 1,8-Diazabicyclo[5.4.0]undec-7-ene (DBU) (22 kg, 5.5 equiv) and the DBU transfer lines were rinsed with $CH_3CN$ (13 L) which was added to the reactor. (II-2) (11.16 kg, 1.1 equiv) was added to the reactor followed by (I-1) (6.78 kg, 95 wt % assay, 1 equiv) to R1. In a second reactor (R2), (benzotriazol-1-yloxy)tris(pyrrolidino)phosphonium hexafluorophosphate (PyBOP) (17.8 kg, 1.30 equiv) was dissolved in $CH_3CN$ (32 L) and added slowly to the batch in R1 while maintaining 15-35° C. R2 was rinsed with $CH_3CN$ (6.5 L) and the rinse was added to R1. The batch was stirred for 15-30 minutes at 15-35° C., then the reaction mixture was sampled for reaction completion IPC (97.7% conversion of (I-1) to Compound A). To a second reactor (R2) is added CPW Charcoal (0.64 kg, 10 wt %) and the batch in R1 is transferred to the charcoal reactor R2. The slurry is stirred at 25° C. for 14.5 hour, then filtered through an inline filter (3M Zeta-Plus HT). R2 and the inline filter are rinsed with $CH_3CN$ (6.5 L×2) and the wash sent to R1. The de-liquored wet-cake is dried inside a vacuum oven at 50° C. for NLT 90 hours to give 11.43 kg crude Compound A free base as a solid, with 83% yield and 98.5% purity.

Example 2D: Alternative Preparation of Compound A From Intermediate (I-1) With PyBOP and DBU, Followed by Recrystallization

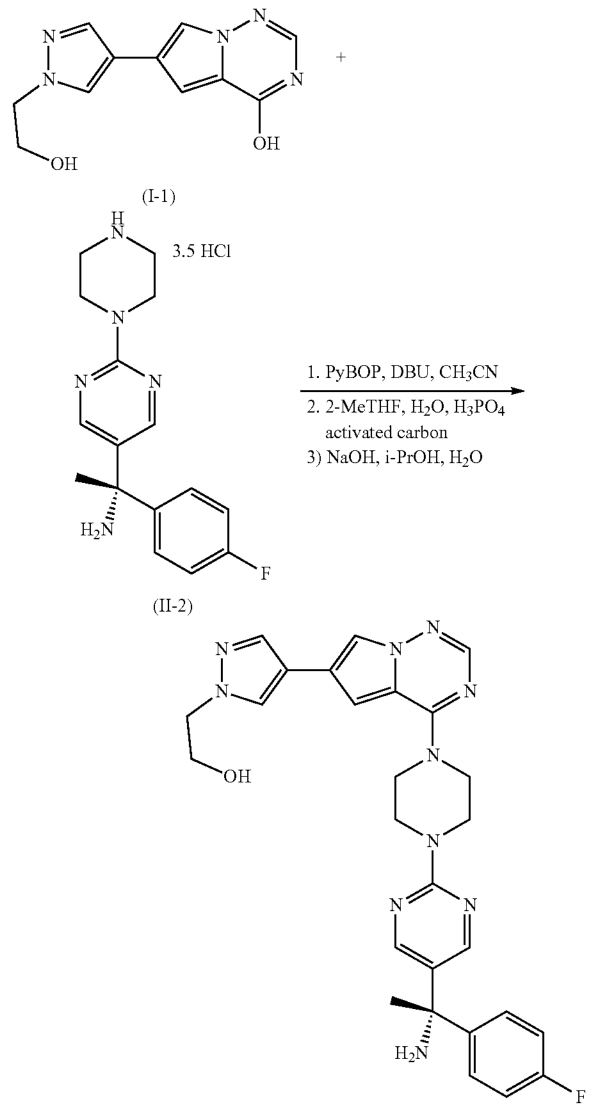

(I-1)

(II-2)

Compound A

To a reactor R1 was charged at 20-32° C. DBU (98.6 g, 5.5 equiv), $CH_3CN$ (240 mL). (II-2) (54.6 g, 70.6 wt % assay in free base, 1.1 equiv). (I-1) (30 g, 95 wt % assay, 1 equiv.) is then added to R1. To a separate reactor R2 was charged PyBOP (79.0 g, 1.30 equiv.) and $CH_3CN$ (150 mL), which was then added slowly to R1 at 25-32° C. The reaction mixture in R1 was stirred at the same temperature until it was judged to be complete by IPC (98.5% conversion at 0.5 h). To the reactor was charged CPW Charcoal (3 g, 10 wt %). The slurry is stirred at 20-25° C. for 1 h, then filtered. R1 and the inline filter are rinsed with $CH_3CN$ (30 mL×2). The filtrate in a separate reactor R3 was seeded with Compound A (0.3 g, 1 wt %), which was followed by addition of water (855 mL) in 1 h at 18-20° C. The slurry was stirred for 18 h at the same temperature, followed by filtration. The wet cake was washed with water (120 mL×2) and then dried to give 54.7 g Compound A. Compound A resulting from the procedure described directly above was further purified. To a reactor R1 was charged water (514 mL), 2-methyl tetrahydrofuran (2-MeTHF) (271 mL) and Compound A (30 g). 85% phosphoric acid ($H_3PO_4$) (7.2 g, 76.3 wt %, 1.1 equiv.) was then added to the solution of Compound A. The mixture was stirred for 0.5 h, followed by filtration into a separate reactor R2. The aqueous layer was separated from the organic layer. The aqueous layer was washed with 2-MeTHF (136 mL×2). To the reactor containing the aqueous layer was charged CPW charcoal (3 g, 10% w/w), which was followed by filtration and washing with water (30 mL). To the reactor containing the filtrate, was added isopropanol (i-PrOH) (120 mL), then 18.2% w/w of a solution prepared from 30% sodium hydroxide (NaOH) (7.77 g) and water (39.3 mL). The mixture was seeded with Compound A (0.3 g, 1 wt %), which was followed by addition of the remainder of NaOH solution. The resulting slurry was stirred at ambient temperature for 1 h, filtered, then washed with water (90 mL). The wet cake was dried under vacuum at 50° C. to give 24 g of Compound A as a solid, with 77% yield, 99.7% HPLC purity, 98.1 wt % by quantitative NMR assay. The recrystallization of Compound A aids in the purging of critical impurities and increases the purity of Compound A (Table 2).

TABLE 2

Purging of Impurities by Recrystallization of Compound A

| Example # | Testing Items | Before recrystallizaiton | After recrystallization |
|---|---|---|---|
| 1 | HPLC purity (a/a) | 95.4% | 99.5% |
| | Impurity 1 | 2.5% | <0.05% |
| | HPLC assay (w/w) | 93.4% | 97.2% |
| 2 | HPLC purity (a/a) | 98.1% | 99.7% |
| | Impurity 2 | 0.68% | <0.05% |
| | Impurity 3 | 0.25 | <0.05% |
| | HPLC assay (w/w) | 91.9% | 97.0% |

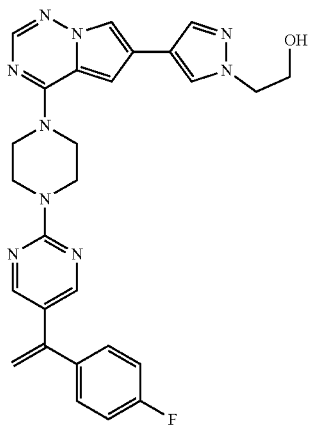 [SMILES: C=C(c1ccc(F)cc1)c1cnc(N2CCN(c3ncnn4cc(-c5cnn(CCO)c5)cc34)CC2)nc1]

Impurity 1

TABLE 2-continued

| Purging of Impurities by Recrystallization of Compound A | | | |
|---|---|---|---|
| Example # | Testing Items | Before recrystallizaiton | After recrystallization |
| 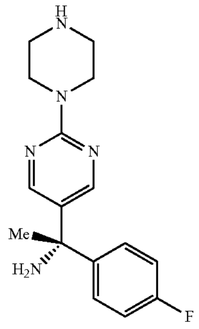 Impurity 2 | | | |
| 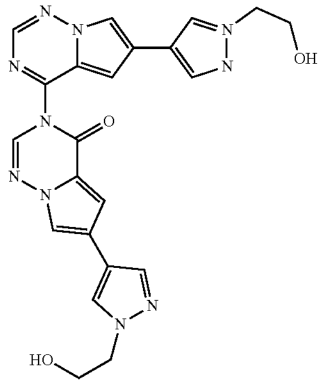 Impurity 3 | | | |

Example 3: Investigation of Coupling Agents and Conditions for the Preparation of Compound A

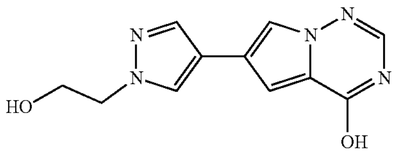

(I-1)

+

-continued

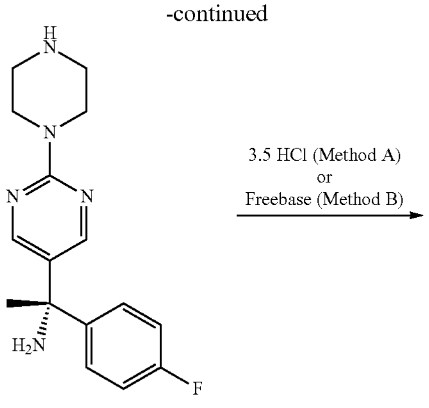

(II-1)

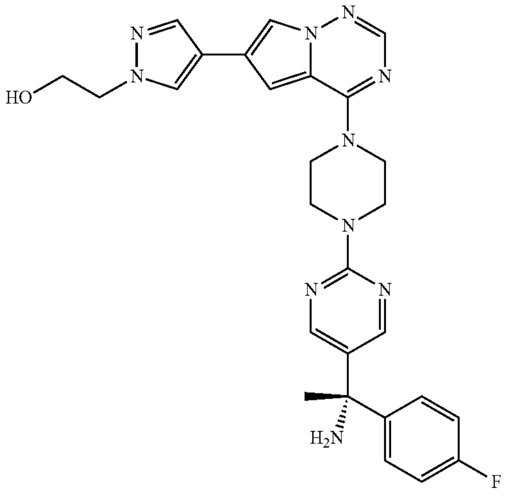

Compound A

Several different coupling agents, bases, and solvents were investigated for the preparation of Compound A. It was discovered herein that certain phosphonium reagents were necessary for successful coupling of I-1 and II-1 to produce Compound A. All other coupling agents investigated did not afford Compound A. More specifically, the results of the conditions that were investigated for the coupling of the first compound (I-1) and the second compound (II-1) (Method A: II-1 as 3.5× HCl salt form (Table 2) and Method B: II-1 as freebase (Table 3) are described below. The experiments were carried out as follows: (I-1) (1.0 g, 1.0 equiv.), an amide coupling reagent (1.5 equiv.) and solvent (15 mL) were charged to a flask (R1) at room temperature. In a separate flask (R2) were combined (11-2 3.5× HCl Salt, Method A; II-1 freebase, Method B) (1.2 equiv.), base and solvent (15 mL) at room temperature. The contents of R2 were added to R1, stirred (at room temperature using Method A and at the target temperature using Method B) and monitored by HPLC. Only PyBOP in preferably, acetonitrile afforded the desired Compound A.

TABLE 3

Summary of results for Compound A using Method A (II-1 3.5 HCl Salt)

| Coupling Reagent | Solvent | Base/amount | Results |
|---|---|---|---|
| PyBOP | $CH_3CN$ | DBU (5.5 equiv) | 100% conversion within 3 h |
| PyBOP | $CH_3CN$:DMF (1:1) | $Et_3N$ (5.5 equiv) | Slow conversion, reaction |
| PyBOP | $CH_3CN$ | DIPEA (5.5 equiv) | stalled |
| PyBOP | DMF | DIPEA (5.5 equiv) | |
| $T_3P$ | $CH_3CN$ | $Et_3N$ (5.5 equiv) | No conversion to Compound A |
| CDMT | $CH_3CN$:DMF (1:1) | NMM (5.5 equiv) | No conversion to Compound A. |
| CDMT | EtOH:$H_2O$ (1:1) | NMM (5.5 equiv) | |
| DMTMM | $CH_3CN$ | NMM (4.0 equiv) | Coupling reagent reacted with II |
| | | | 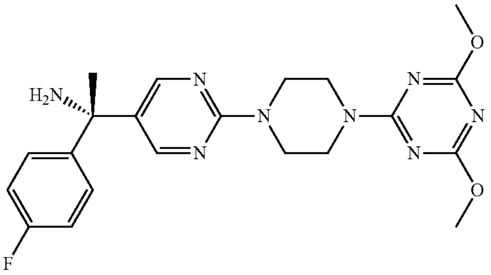 [SMILES: COc1nc(OC)nc(N2CCN(c3ncc([C@@](C)(N)c4ccc(F)cc4)cn3)CC2)n1] |
| EDCI | DMF | $Et_3N$ (5.5 equiv) | No conversion to Compound A |

PyBOP: benzotriazol-1-yloxytripyrrolidinophosphonium hexafluorophosphate
$T_3P$: Propanephosphonic acid anhydride
CDMT: 2-Chloro-4,6-dimethoxy-1,3,5-triazine
DMTMM: 4-(4,6-Dimethoxy-1,3,5-triazin-2-yl)-4-methylmorpholinium chloride
EDCI: 1-Ethyl-3-(3-dimethylaminopropyl)carbodiimide
DBU: Diazabicycloundecene
$Et_3N$: Triethylamine
DIPEA: Diisopropylethylamine
NMM: N-Methylmorpholine

TABLE 4

Summary of results for Compound A using Method B (II-1 freebase)

| Coupling Reagent | Solvent | Base/amount | Temp (° C.) | Results |
|---|---|---|---|---|
| EDCI | DCM | DMAP (2.5 equiv) | 40 | No conversion to Compound A |
| EDCI | DMF | DMAP (2.5 equiv) | RT | |
| EDCI | DCM | DMAP (2.5 equiv) | 40 | |
| EDCI | DMF | DMAP (2.5 equiv) | RT | |
| EDCI | $CH_3CN$ | DBU (2.5 equiv) | RT | |
| CDI | $CH_3CN$ | DBU (2.5 equiv) | 40 | No conversion to Compound A. Formed Compound A + carbon monoxide |
| HATU | $CH_3CN$ | DBU (2.5 equiv) | 40 | No conversion to Compound A |
| PyBOP | $CH_3CN$ | DBU (0.2 equiv) | 40 | No conversion to Compound A, catalytic DBU was ineffective |
| PyBOP | CH3CN | DIPEA (2.5 equiv) | 60 | 100% conversion in 5 hours |
| PyBOP | DCE | DIPEA (2.5 equiv) | 60 | 85% conversion in 4 hours, increased impurities |
| PyBOP | THF | DIPEA (2.5 equiv) | 60 | 90% conversion in 4 hours, increased impurities |
| PyBOP | $CH_3CN$ | DIPEA (2.5 equiv) + | 40 | 98% conversion after 12 hours |
| PyBOP | $CH_3CN$ | DMAP (0.1 equiv) | 55 | Reaction stalled at 55% conversion |
| PyBOP | 2-MeTHF | | 40 | No conversion to Compound A |
| PyBOP | $CH_3CN$ | DMAP (2.5 equiv) | 40 | 100% conversion after 12 hours |

TABLE 4-continued

Summary of results for Compound A using Method B (II-1 freebase)

| Coupling Reagent | Solvent | Base/amount | Temp (° C.) | Results |
|---|---|---|---|---|
| PyBOP | 1,4-dioxane | $Et_3N$ (2.5 equiv) | 45 | 75% conversion after 12 hours |
| PyBOP | | Pyridine (30 vol) | 45 | No conversion to Compound A |

PyBOP: benzotriazol-1-yloxytripyrrolidinophosphonium hexafluorophosphate
EDCI: 1-Ethyl-3-(3-dimethylaminopropyl)carbodiimide
CDI: 1,1'-Carbonyldiimidazole
HATU: (1-[Bis(dimethylamino)methylene]-1H-1,2,3-triazolo[4,5-b]pyridinium 3-oxide hexafluorophosphate
DCE: 1,2-dichloroethane
DBU: Diazabicycloundecene
$Et_3N$: Triethylamine
DIPEA: Diisopropylethylamine
DMAP: 4-Dimethylaminopyridine
RT: room temperature

Example 4: Use of TEA in Combination With PyClOP and PyBOP

Several bases such as DIPEA, DMAP, DABCO, N-methylmorpholine and potassium carbonate were tried for the coupling of the first compound (I-1) and the second compound (II-1) with limited success. Only trace amounts of the desired product, Compound A, were observed when DABCO, N-methylmorpholine, and potassium carbonate were used at 50° C. DMAP and DIPEA showed low conversion rates of a/a I-1 around 40% at 50° C. and problems were encountered with DIPEA in acetronitrile due to 1) the biphasic nature of the reaction mixture, and oiling after addition of water that makes isolation of Compound A challenging. TEA and DBU were both identified as suitable non-nucleophilic bases for the coupling reaction in combination with PyClOP and PyBOP.

TEA was ultimately found to be the non-nucleophilic base that afforded the best results with PyClOP. TEA has the advantage of being mixable with acetonitrile. The precipitation of TEA hydrochloride during the reaction offers an advantage because it can be easily removed by filtration prior to crystallization of the product. The combination of PyClOP and TEA resulted in cleaner reaction profiles and better control of critical impurities (Table 4).

TABLE 4

Comparison of Compound A Purity Prepared with PyBOP/DBU vs PyClOP/TEA

| Entry | Coupling Reagent | Base | Compound A (%-a/a) | Impurity 1 (%-a/a) | Impurity 2 (%-a/a) | Impurity 3 (%-a/a) | Impurity 4 (%-a/a) | LUI* |
|---|---|---|---|---|---|---|---|---|
| 1 | PyBOP 1.3 eq | DBU 5.5 eq | 97.4 | 1.8 | <0.05 | 0.11 | 0.21 | 0.27 |
| 2 | PyClOP 1.3 eq | DBU 5.5 eq | 97.3 | 0.99 | 0.09 | 0.11 | 0.24 | 0.76 |
| 3 | PyClOP 1.6 eq | TEA 9.5 eq | 98.6 | 0.39 | <0.05 | 0.30 | 0.16 | 0.13 |

*LUI = Largest unknow impurity

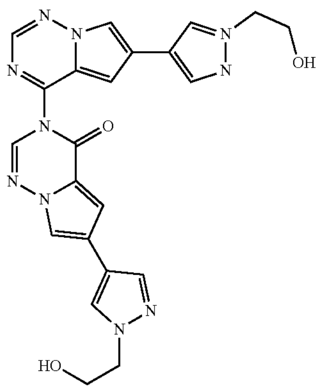

Impurity 1

TABLE 4-continued
| Comparison of Compound A Purity Prepared with PyBOP/DBU vs PyCIOP/TEA | | | | | | | | |
|---|---|---|---|---|---|---|---|---|
| Entry | Coupling Reagent | Base | Compound A (%-a/a) | Impurity 1 (%-a/a) | Impurity 2 (%-a/a) | Impurity 3 (%-a/a) | Impurity 4 (%-a/a) | LUI* |
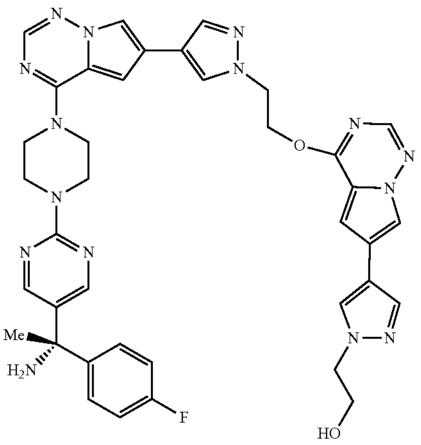
Impurity 2
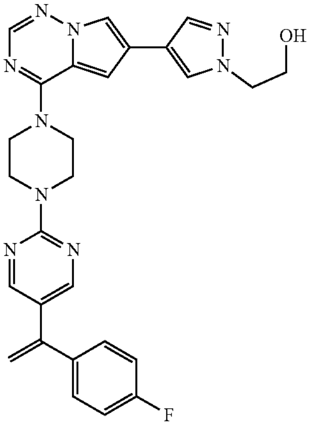
Impurity 3

TABLE 4-continued

Comparison of Compound A Purity Prepared with PyBOP/DBU vs PyClOP/TEA

| Entry | Coupling Reagent | Base | Compound A (%-a/a) | Impurity 1 (%-a/a) | Impurity 2 (%-a/a) | Impurity 3 (%-a/a) | Impurity 4 (%-a/a) | LUI* |
|---|---|---|---|---|---|---|---|---|

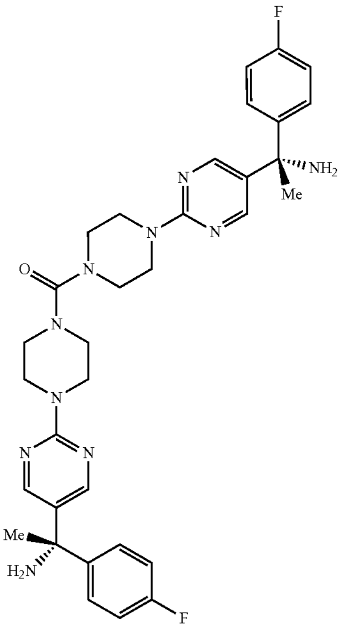

Impurity 4

What is claimed is:

1. A method of preparing Compound A:

Compound A

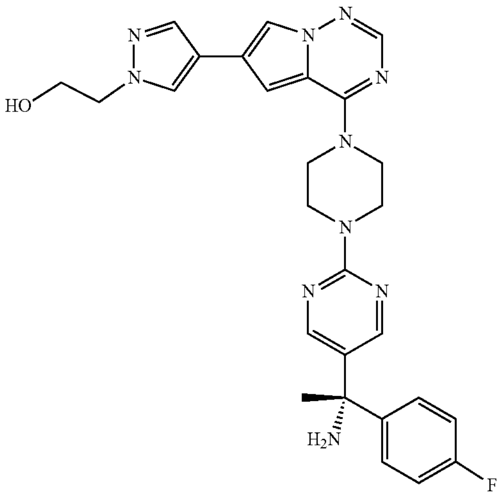

comprising reacting a first compound represented by formula (I-1) or a pharmaceutically acceptable acid salt thereof:

(I-1)

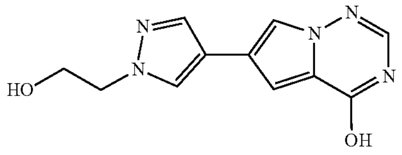

and a second compound represented by formula (II-1) or a pharmaceutically acceptable acid salt thereof:

(II-1)

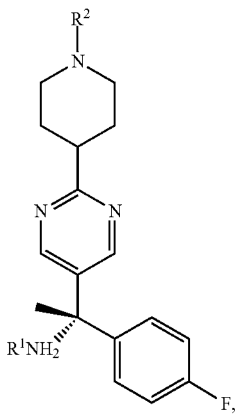

wherein $R^1$ and $R^2$ are each independently selected from H and an amine protecting group, and cleaving the $R^1$ and $R^2$ amine protecting groups, if present, to form Compound A.

2. The method of claim 1, wherein $R^2$ is H and $R^1$ is $S(=O)C(CH_3)_3$; or wherein $R^2$ is $C(O)OC(CH_3)_3$ and $R^1$ is $S(=O)C(CH_3)_3$.

3. The method of claim 1, wherein the reaction is mediated by an agent that activates the aromatic hydroxyl group in the first compound (I-1) for nucleophilic displacement.

4. The method of claim 3, wherein the agent is a phosphonium salt selected from the group consisting of (benzotriazol-1-yloxy)tris(dimethylamino)phosphonium hexafluorophosphate (BOP), (benzotriazol-1-yloxy)tris(pyrrolidino) phosphonium hexafluorophosphate (PyBOP), chlorotripyrrolidinophosphonium hexafluorophosphate (PyClOP), 2-(benzotriazol-1-yloxy)-1,3-dimethyl-2-pyrrolidin-1-yl-1,3-diazaphospholidinium hexafluorophosphate (BOMP), (7-azabenzotriazol-1-yloxy)tris(di-methylamino) phosphonium hexafluorophosphate (AOP), (7-azabenzotriazol-1-yloxy)tris(pyrrolidino)phosphonium hexafluorophosphate (PyAOP), 1-cyano-2-ethoxy-2-oxoethylideneaminooxy-tris-pyrrolidino-phosphonium hexafluorophosphate (PyOxim), and bromotripyrrolidinophosphonium hexafluorophosphate (PyBrOP).

5. The method of claim 4, wherein the agent is (benzotriazol-1-yloxy)tris(pyrrolidino)phosphonium hexafluorophosphate (PyBOP); or the agent is chlorotripyrrolidinophosphonium hexafluorophosphate (PyClOP).

6. The method of claim 3, comprising reacting in the presence of a non-nucleophilic base.

7. The method of claim 6, wherein the non-nucleophilic base is an amine non-nucleophilic base.

8. The method of claim 7, wherein the amine non-nucleophilic base is 1,8-diazabicyclo(5.4.0)undec-7-ene (DBU); or the amine non-nucleophilic base is triethylamine (TEA).

9. The method of claim 6, wherein the second compound is a pharmaceutically acceptable acid salt of the compound of formula (II-1); or wherein the second compound is the free base of the compound of formula (II-1).

10. The method of claim 9, wherein the amine non-nucleophilic base is present in a molar excess relative to the moles of the first compound (I-1).

11. The method of claim 6, wherein the first compound (I-1) and the second compound (II-1) are dissolved in a first solvent to form a solution.

12. The method of claim 11, wherein the first solvent is selected from the group consisting of acetonitrile ($CH_3CN$), dimethylformamide (DMF), 2-methyl tetrahydrofuran (2-MeTHF), tetrahydrofuran (THF), dichloroethane (DCE), dioxane and dimethylaminopyridine (DMAP).

13. The method of claim 11, wherein reacting is conducted at a temperature of 15-100° C.

14. The method of claim 13, wherein the temperature is 20-30° C. when PyBOP is the activating agent and the non-nucleophilic base is DBU; or the temperature is 80-90° C. when PyClOP is the activating agent and the non-nucleophilic base is TEA.

15. The method of claim 11, wherein the agent is added to the solution of the first compound (I-1) and the second compound (II-1) dissolved in the first solvent.

16. The method of claim 11, wherein the non-nucleophilic amine base is added prior to the additional addition of the first solvent.

17. The method of claim 9, wherein the pharmaceutically acceptable acid salt of compound of formula (II-1) is an HCl salt.

18. The method of claim 10, wherein the amine non-nucleophilic base is present in a 5.0 to 12.0 molar excess relative to the moles of the first compound (I-1).

* * * * *